US007601492B2

(12) United States Patent
Fu et al.

(10) Patent No.: US 7,601,492 B2
(45) Date of Patent: Oct. 13, 2009

(54) GENOME MAPPING OF FUNCTIONAL DNA ELEMENTS AND CELLULAR PROTEINS

(75) Inventors: Xiang-Dong Fu, San Diego, CA (US); Young-Soo Kwon, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 303 days.

(21) Appl. No.: 10/561,764

(22) PCT Filed: Jul. 2, 2004

(86) PCT No.: PCT/US2004/021450

§ 371 (c)(1),
(2), (4) Date: Aug. 2, 2006

(87) PCT Pub. No.: WO2005/007814

PCT Pub. Date: Jan. 27, 2005

(65) Prior Publication Data

US 2007/0059703 A1    Mar. 15, 2007

Related U.S. Application Data

(60) Provisional application No. 60/485,052, filed on Jul. 3, 2003.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

2001/0049102 A1 *  12/2001  Huang et al. .................... 435/6
2002/0172946 A1     11/2002  Jian-Bing et al.
2004/0209299 A1     10/2004  Pinter
2008/0125328 A1 *   5/2008   Wyrick et al. .................. 506/9

FOREIGN PATENT DOCUMENTS

WO    WO 89/09835     10/1989
WO    WO 01/16378     3/2001

OTHER PUBLICATIONS

Ahern, The Scientist 9 (15), 20 (1995).*
Aviva Systems Biology: "ChIP-GLAS Complete product handbook for the Aviva Systems Biology ChIP-GLAS system" [online] 2005, pp. 1-29 (URL:www.avivasysbio.com/corp/ChIP-GLAS%20Manual%20H20Klpdf).
Barany F., "The Ligase Chain Reaction In A PCR World," *PCR Methods and Applications*, Cold Spring Harbor, NY, U.S.A. vol. 1, No. 1, pp. 5-16, 1991.
Fan et al., "A versatile assay for high-throughput gene expression profiling on universal array matrices," *Genome Research* 14(5):878-885, 2004.
Nal et al., "Location analysis of DNA-bound proteins at the whole-genome level: Untangling transcriptional regulatory networks," *Bioessays* 23(6):473-476, 2001.
Yeakley et al., "Profiling alternative splicing on fiber-optic arrays," *Nature Biotechnology* 20(4):353-358, 2002.

* cited by examiner

*Primary Examiner*—James Martinell
(74) *Attorney, Agent, or Firm*—Joseph R. Baker, Jr.; Gavrilovich, Dodd & Lindsey LLP

(57) ABSTRACT

The disclosure provides methods of examining the binding of proteins to DNA across a genome (e.g., the entire genome or a portion thereof, such as one or more chromosomes or a chromosome regions). In particular, the disclosure relates to a method of identifying a regulatory region (e.g., a protein or enhancer region) of genomic DNA to which a protein of interest binds. In one aspect, the disclosure looks at tissue related regulation. In another aspect, the disclosure looks at developmental related regulation. In yet another aspect, the disclosure looks at regulation of expression in a particular disease state or disorder.

35 Claims, 11 Drawing Sheets

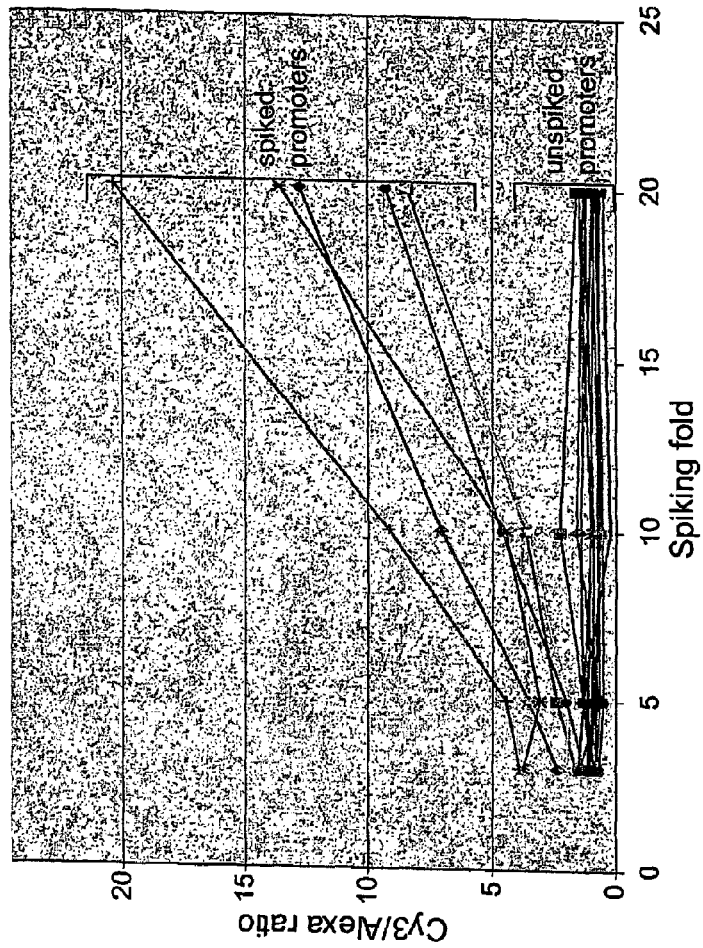
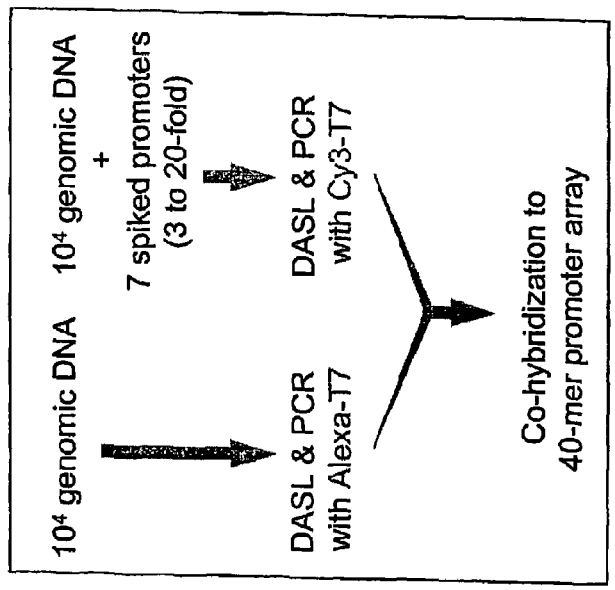
FIG. 3B

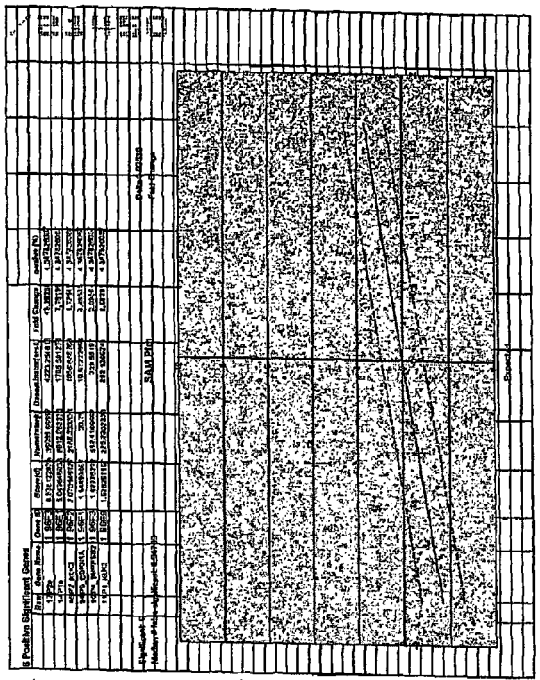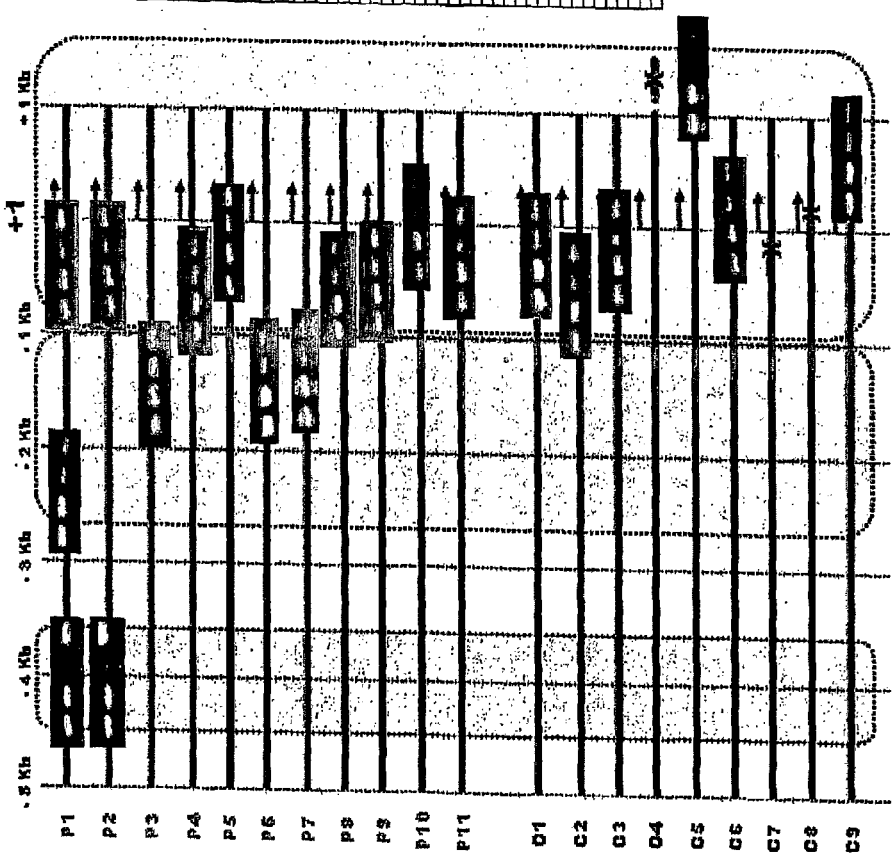
FIG. 4

Identification of Estrogen Receptor Target Genes by DASL
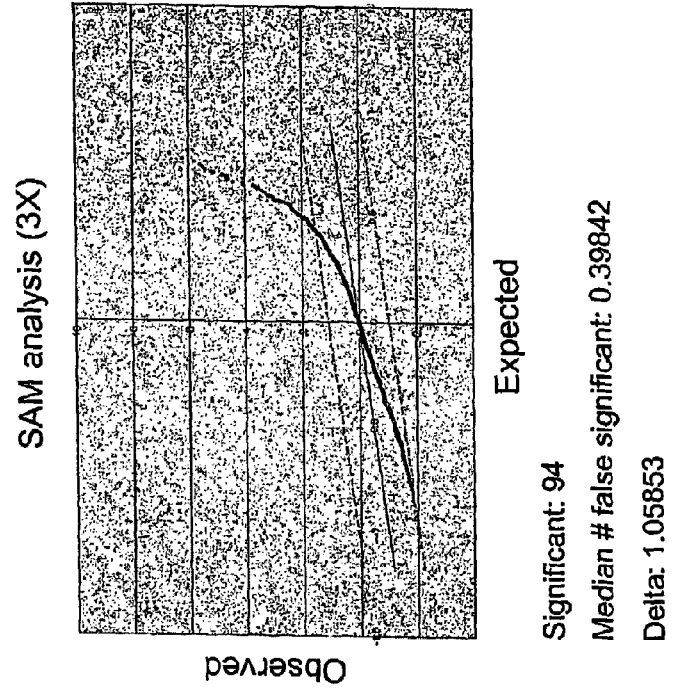
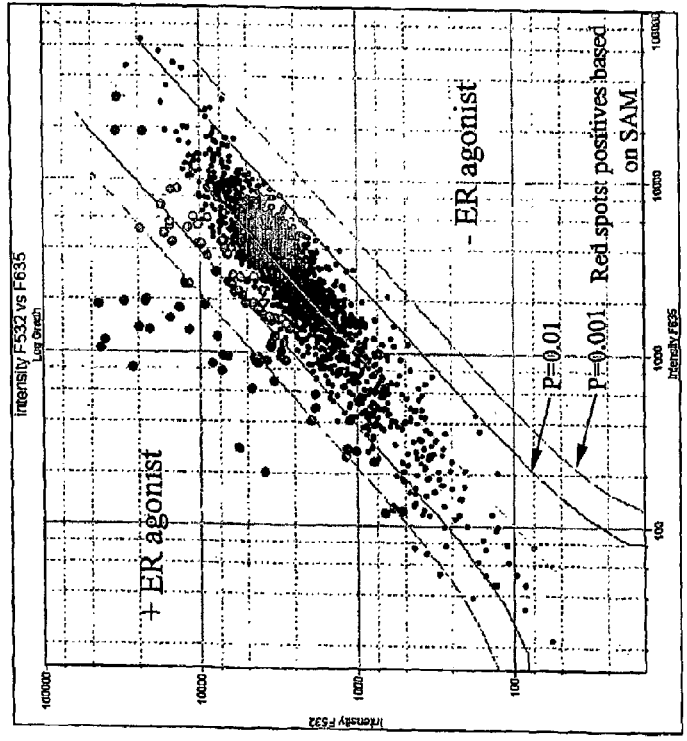
FIG. 6

GENOME MAPPING OF FUNCTIONAL DNA ELEMENTS AND CELLULAR PROTEINS

CROSS REFERENCE TO RELATED APPLICATION

This disclosure is filed under 35 U.S.C. §371 and claims priority to International Application Ser. No. PCT/US2004/021450, filed Jul. 2, 2004, which claims priority under 35 U.S.C. §119 to provisional application Ser. No. 60/485,052, filed Jul. 3, 2003, the disclosures of which are incorporated herein by reference.

STATEMENT REGARDING FEDERALLY SPONSORED RESEARCH

The invention was funded in part by Grant No. 5R33CA88351 awarded by the National Institutes of Health. The government has certain rights in the invention.

TECHNICAL FIELD

This disclosure relates to mapping of proteins and DNA element in a genome.

BACKGROUND

Transcriptional regulation involves a large number of proteins or protein complexes specifically assembled at a given promoter to activate or suppress RNA synthesis. In a specific tissue or cell type, a promoter can be turned on by a sequence of specific recognition events. Transcription factors bind cis-acting regulatory sequences; these DNA binding proteins then recruit co-activator complexes and these pre-activation complexes then recruit the core transcription machinery. Such a sequential recruitment mechanism was demonstrated on the HO gene promoter during the cell cycle in yeast (Cosma et al., 1999). Similarly, a gene can be turned off by the recruitment of transcription co-repressor complexes through sequence-specific DNA binding proteins during repression involved chromatin remodeling factors that modify histones and a long term molecular memory may be established by epigenetic modification of a specific chromatin region(s) via DNA methylation.

An advance in achieving progress in understanding the area of DNA binding proteins is the chromatin immunoprecipitation (ChIP) assay. This technology enables mapping of functional DNA elements that are engaging in interactions with specific DNA binding proteins and their associated protein complexes in vivo and has been applied to many individual case studies. In principle, this approach could lend itself to high-throughput detection methods, which would open up new opportunities for systems-level approaches to gene regulatory networks.

Researcher are seeking to identify various functional DNA elements embedded in the human genome, whether or not they are involved in gene expression, DNA replication, or establishment of chromosome territories in the cell. The method ideally suited for achieving the goal is the so-called ChIP-on-Chip technology, which is the ChIP assay coupled with high throughput detection on chips containing a microarray of human promoters.

The ChIP assay has been widely used in localizing in vivo binding sites for transcription factors. Referring to FIG. 1A, briefly, cultured cells are treated with formaldehyde to induce crosslinking between DNA and bound proteins in vivo. Treated cells are disrupted and nucleoproteins are recovered. Sonication is then used to randomly shear DNA into ~0.5 kb pieces. Because of covalent linkage induced by crosslinking, specific proteins remain associated with fragmented DNA. Specific antibodies against target proteins are used to immunoprecipitate DNA-protein complexes. Both starting and immunoprecipitated materials are analyzed by PCR using primers specific for a given DNA region(s) under investigation. A specific in vivo interaction can be inferred if immunoprecipitation results in a significant enrichment of the DNA fragment(s) in question.

The ChIP assay has been used to detect specific targets for transcription and DNA replication factors, chromatin remodeling factors, modified histones, methylated DNA, and the like. Furthermore, the assay has also been used to detect specific association of RNA binding proteins with DNA elements bridged by transcribing RNA because transcription and splicing are known to be spatially and temporarily coupled in the cell.

The ChIP-on-Chip technology has been used to address detailed mechanistic question on selected DNA target(s). However, starting and immunoprecipitated materials have to be analyzed by PCR one at a time, which requires the selection of a target set based on available functional information. Briefly, using information from sequenced and annotated yeast genomes, individual intragenic sequences are PCR-amplified and spotted on glass to form a promoter microarray. Immunoprecipitated DNA fragments are linked by ligation with a primer-landing site on both ends, thereby permitting signal amplification by PCR (i.e., ligation-mediated PCR or LM-PCR). PCR amplified and immunoprecipitated materials are finally labeled with different fluorescence dye by random priming. Pooled PCR products are then hybridized to the promoter array to detect which promoters are specifically enriched by chromatin immunoprecipitation.

Referring to FIG. 1B, the ChIP-on-Chip technology requires $10^8$ cells in each experiment, thus precluding analysis of development, tumorgenesis and stem cells where starting materials may be limited. In addition, microarray-based approaches will face the specificity issue. A schematic description of ChIP-on-Chip is presented in FIGS. 1A-1B and a summary comparison in Table 1, below.

SUMMARY

The disclosure provides a method of detecting a polynucleotide-polypeptide interaction domain in a genome of an organism, comprising a) immunoprecipitating polynucleotides linked to a polypeptide; b) dissassociating the polynucleotide and polypeptide; c) contacting the polynucleotide with a primer pair under conditions whereby the primer pair hybridize to the polynucleotide to form a first hybridization complex, each primer comprising at least two portions, a first portion comprising a target-specific oligonucleotide that is capable of hybridizing to a target polynucleotide, and a second portion comprising a universal primer landing site, wherein the universal landing sites are not the same, d) contacting the first hybridization complex with a ligase under conditions whereby primer pairs hybridized to the polynucleotide are ligated to form a ligated probe; e) amplifying the ligated probe with universal primers to generated an amplified-labeled product; f) contacting the amplified-labeled product with an array of oligonucleotides to form assay complexes; and g) detecting said assay complexes, wherein the presence of complexes is indicative of DNA that binds the immunoprecipitated polypeptide.

The disclosure also provides a method of identifying a region of a genome of a living cell to which a polypeptide of interest binds, comprising the steps of: a) crosslinking DNA binding protein in the living cell to genomic DNA of the living cell, thereby producing protein-DNA complexes comprising DNA binding polypeptide crosslinked to genomic DNA; b) generating DNA fragments of the protein-DNA complexes in a), thereby producing a mixture comprising DNA fragments to which DNA binding protein is bound; c) removing a DNA fragment to which a polypeptide of interest is bound from the mixture produced in b); d) separating the DNA fragment of c) from the polypeptide of interest; e) contacting the DNA with a primer pair under conditions whereby primer pair hybridize to the DNA to form a first hybridization complex, each primer comprising at least two portions, a first portion comprising a target-specific oligonucleotide that is capable of hybridizing to a target polynucleotide, and a second portion comprising a universal primer landing site, the two primers are designed to be specific for an upstream and downstream segment of a target polynucleotide, wherein the universal landing sites are not the same; f) contacting the first hybridization complex with a ligase under conditions whereby primer pairs hybridized to the polynucleotide are ligated to form a ligated probe; g) amplifying the ligated probe of f); h) combining the amplified product of g) with DNA comprising a sequence complementary to genomic DNA of the cell, under conditions in which hybridization between the amplified product and a region of the sequence complementary to genomic DNA occurs to form a second hybridization complex; and i) identifying the second hybridization complex of h), wherein the second hybridization complex comprises the region of the genome in the cell to which the polypeptide of interest binds.

The disclosure further provides a method of identifying a region of a genome of a living cell to which a polypeptide of interest binds, comprising: a) crosslinking DNA binding polypeptides in the living cell to genomic DNA of the living cell, thereby producing a protein-DNA complex comprising DNA binding polypeptides crosslinked to genomic DNA; b) generating DNA fragments of the protein-DNA complex, thereby producing DNA fragments to which DNA binding polypeptides are bound; c) immunoprecipitating the DNA fragment produced using an antibody that specifically binds the polypeptide of interest; d) separating the DNA fragment identified in c) from the polypeptide of interest; e) contacting the DNA with a primer pair under conditions whereby the primer pair hybridize to the DNA to form a first hybridization complex, each primer comprising at least two portions, a first portion comprising a target-specific oligonucleotide that is capable of hybridizing to a target polynucleotide, and a second portion comprising a universal primer landing site, the two primers are designed to be specific for an upstream and downstream segment of a target polynucleotide, wherein the universal landing sites are not the same; f) contacting the first hybridization complex with a ligase under conditions whereby primer pairs hybridized to the polynucleotide are ligated to form a ligated probe; g) amplifying the ligated probe of f) using universal primers labeled with a detectable label; h) combining the amplified product of g) with DNA comprising a sequence complementary to genomic DNA of the cell, under conditions in which hybridization between the amplified product and a region of the sequence complementary to genomic DNA occurs to form a second hybridization complex; i) identifying the second hybridization complex of h) using methods specific for the label, wherein the second hybridization complex comprises the region of the genome in the cell to which the polypeptide of interest binds; and j) comparing the label intensity/amount measured in i) to the amount/intensity of a control, wherein amount/intensity of the label in a region of the genome which is greater than the amount/intensity of label of the control in the region indicates the region of the genome in the cell to which the polypeptide of interest binds.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

FIG. 3A-B show assay results demonstrating the specificity and sensitivity of the method of the disclosure.

FIG. 4 shows the results of ChIP-DASL using androgen responsive promoters in LNCaP cells accompanied by SAM analysis. Each of the gels comprises pairs of input DNA in the presence and absence of androgen (IN+ and IN−) and enriched in the presence and absence of androgen (EN+ and EN−).

FIG. 6 shows identification of estrogen receptor target genes using the methods of the disclosure. Shown is the process in the presence and absence of an estrogen agonist. Also shown is the SAM analysis of the chip data.

FIG. 8 shows the mapping of transcriptional units by tiling on the beta-globulin locus. Shown is the sensitivity of the ChIP-DASL method compared to ChIP-Chip.

DETAILED DESCRIPTION

As used herein and in the appended claims, the singular forms "a," "and," and "the" include plural referents unless the context clearly dictates otherwise. Thus, for example, reference to "a probe" includes a plurality of such cells and reference to "the primer" includes reference to one or more primers and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Understanding how DNA-binding proteins control global gene expression, chromosomal replication and cellular proliferation would be facilitated by identification of the chromosomal locations at which DNA binding proteins function in vivo. Described herein is a genome-wide mapping method for regulated DNA elements and protein regulators.

A procedure referred to as RASL (for RNA Annealing Selection and Ligation) has been employed to address the specification issue generally associated with microarray approaches. In a 5' alternative splicing event, for example, there are two 5' splice sites in competition with a common 3' splice site. Three oligos are used to target to 20 nucleotide exonic sequences at each splice site junction as diagrammed. In order to distinguish between the two competing 3' splice sites, a unique 20 nucleotide index sequence to each 5' oligo (1 or 2, labeled with red and green, respectively). The RASL assay includes the following processes: (1) Annealing, (2) Solid phase selection, (3) Ligation, (4) PCR amplification, and (5) Detection on a universal index array.

Figure 2:
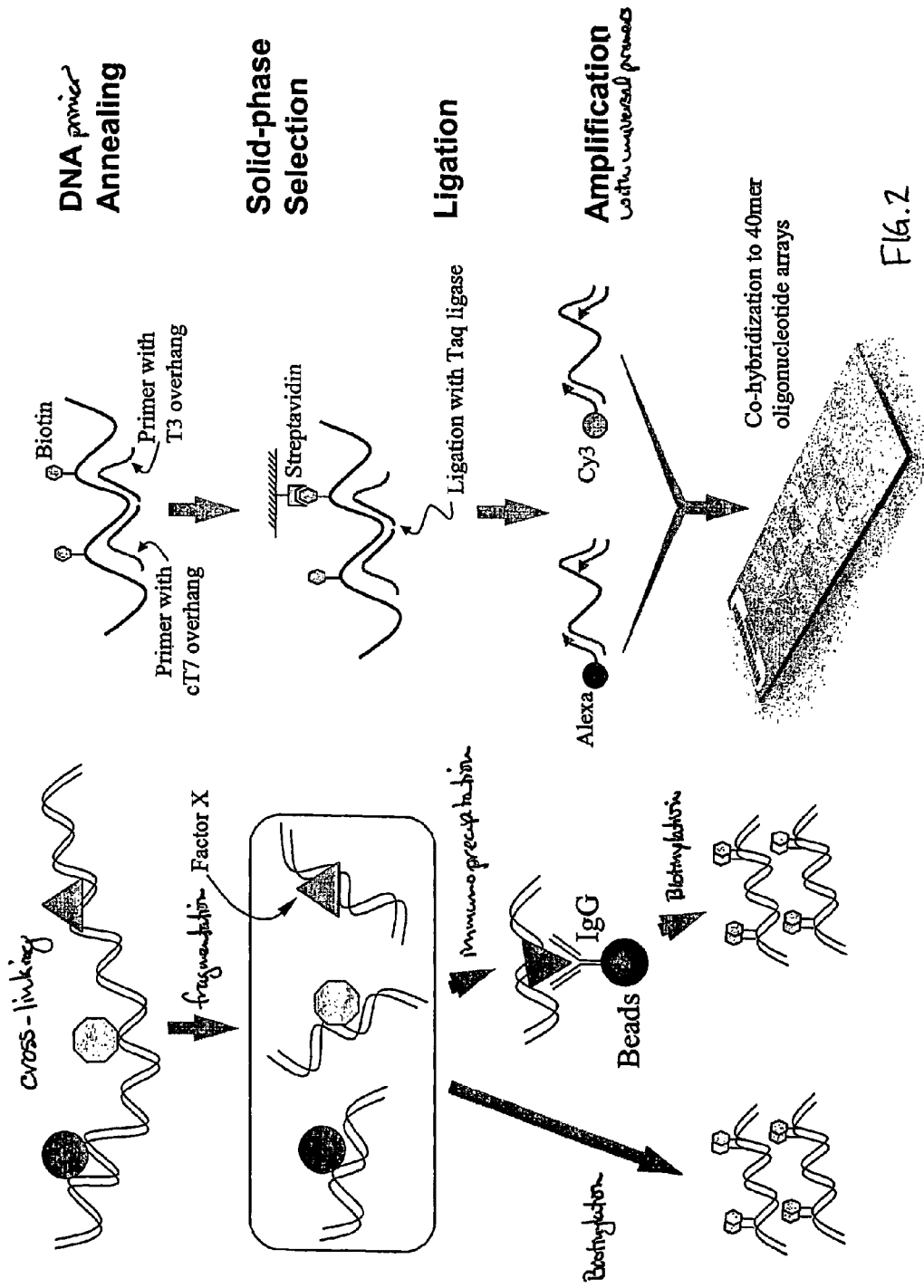
FIG. 2 depict a general process of the disclosure. Shown are cross-linking, fragmentation, immunoprecipitation, biotinylation, primer annealing, solid-phase selection, ligation, amplification and chip analysis.

The disclosure utilizes RNA Annealing Selection and Ligation (RASL) technology in combination with ChIP-on-Chip technology. This combination is referred to herein as "ChIP-DASL". An embodiment of the ChIP-DASL method is provided in FIG. 2.

The disclosure provides methods of examining the binding of proteins to DNA across a genome (e.g., the entire genome or a portion thereof, such as one or more chromosomes or a chromosome regions). In one aspect, the disclosure provides a method of identifying a regulatory region (e.g., a promoter or enhancer region) of genomic DNA to which a protein of interest binds. In another aspect, the disclosure looks at tissue related regulation. In yet another aspect, the disclosure looks at developmental related regulation. In a further aspect, the disclosure looks at regulation of expression in a particular disease state or disorder.

The methods of the disclosure also provide the ability to determine whether a binding protein is a transcription factor. As discussed above, the polynucleotide (e.g. DNA) to which the binding protein interacts are hybridized to genomic fragments (e.g., on a chip). If a ligated probe binds to a genomic fragment on a chip and the genomic fragment on the chip is known to be a regulatory region in the genome of the organism, then the polynucleotide corresponding to the ligated probe is identified as a regulatory region and the protein of interest is a transcription factor.

The methods of the disclosure can be used to examine and/or identify DNA binding proteins across the entire genome of a eukaryotic organism. A variety of DNA binding proteins which bind to DNA can be analyzed. For example, any protein involved in DNA replication or transcription regulation can be examined by the methods of the disclosure.

In another method for identification and isolation of regulatory regions, enrichment of regulatory DNA takes advantage of the fact that the chromatin of actively-transcribed genes generally comprises acetylated histones. See, for example, Wolffe et al., Cell 84:817-819, 1996. In particular, acetylated H3 and H4 are enriched in the chromatin of transcribed genes, and chromatin comprising regulatory sequences is selectively associated with acetylated H3. Accordingly, chromatin immunoprecipitation using antibodies to acetylated histones, particularly acetylated H3, can be used to obtain collections of sequences enriched in regulatory DNA. Examples of such antibodies include, but are not limited to, Anti Acetylated Histone H3, available from Upstate Biotechnology, Lake Placid, N.Y.

Such methods generally involve fragmenting chromatin and then contacting the fragments with an antibody that specifically recognizes and binds to acetylated histones, particularly H3. The polynucleotides from the immunoprecipitate can subsequently be collected from the immunoprecipitate. Prior to fragmenting the chromatin, one can optionally crosslink the acetylated histones to adjacent DNA. Crosslinking of histones to the DNA within the chromatin can be accomplished according to various methods. One approach is to expose the chromatin to ultraviolet irradiation (Gilmour et al., Proc. Nat'l. Acad. Sci. USA 81:4275-4279, 1984). Other approaches utilize chemical crosslinking agents. Suitable chemical crosslinking agents include, but are not limited to, formaldehyde and psoralen (Solomon et al., Proc. Natl. Acad. Sci. USA 82:6470-6474, 1985; Solomon et al., Cell 53:937-947, 1988).

Identification of a binding site for a particular defined transcription factor in cellular chromatin is indicative of the presence of regulatory sequences. This can be accomplished, for example, using the technique of chromatin immunoprecipitation. This technique involves the use of a specific antibody to immunoprecipitate chromatin complexes comprising the corresponding antigen (in this case, a transcription factor of interest), and examination of the nucleotide sequences present in the immunoprecipitate. Immunoprecipitation of a particular polynucleotide bound to an antigen by the antibody is indicative of interaction of the antigen with a polynucleotide (e.g., regulatory domain) (O'Neill et al., in Methods in Enzymology, Vol. 274, Academic Press, San Diego, 1999, pp. 189-197; Kuo et al., Method 19:425-433, 1999; and Current Protocols in Molecular Biology, F. M. Ausubel et al., eds., Current Protocols, Chapter 21, a joint venture between Greene Publishing Associates, Inc. and John Wiley & Sons, Inc., (1998 Supplement)).

Figure 1A:
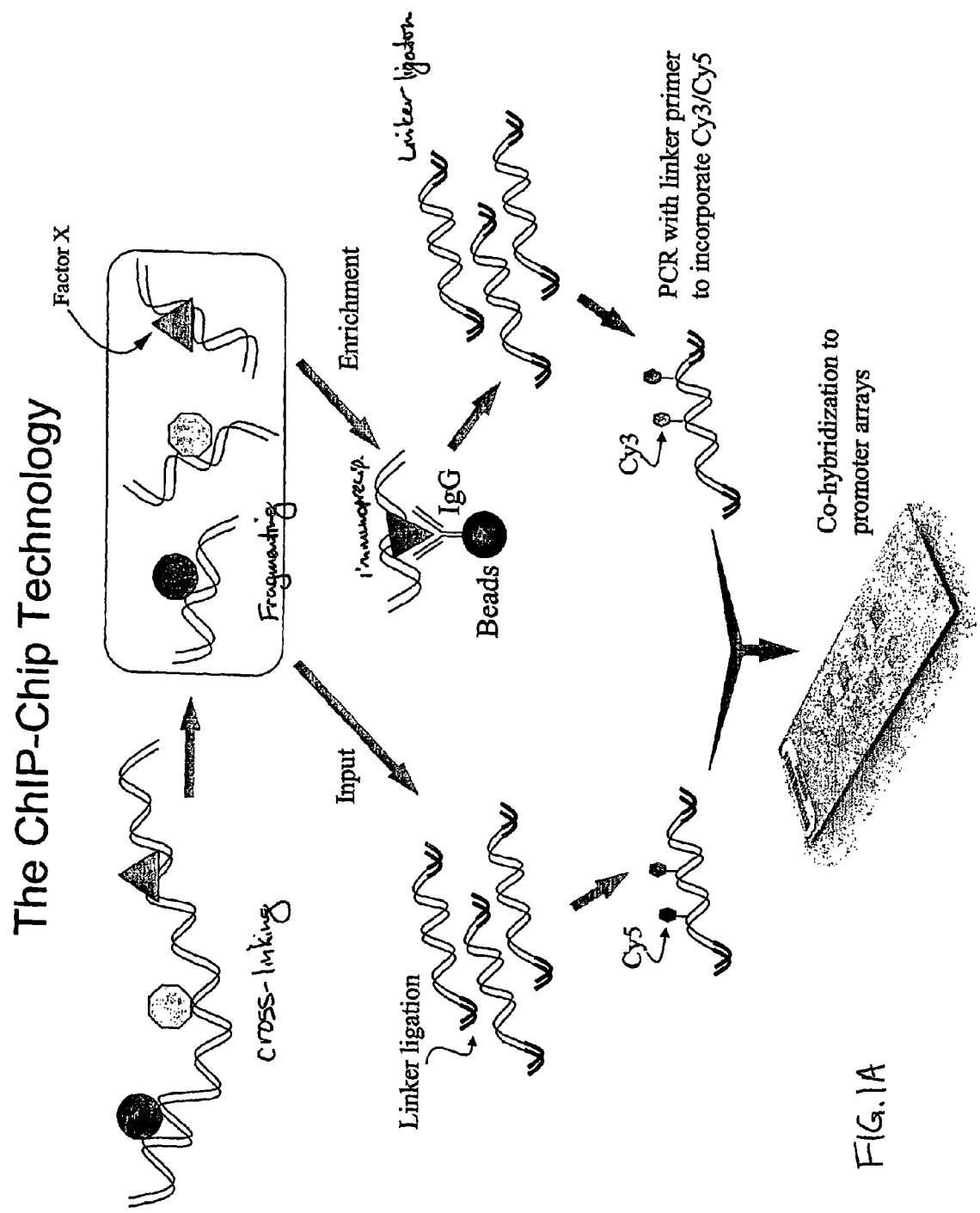
FIG. 1A-B shows a ChIP-on-Chip technique. (A) depicts the process of cross-linking, fragmentation, chromatin immunoprecipitation, linker-ligation, amplification and Chip analysis; (B) shows some of the difficulties with ChIP-on-CHIP including the generation of false positives by hybridization of common repeats and false negatives by cross-hybridization of common repeats.
Figure 1B:
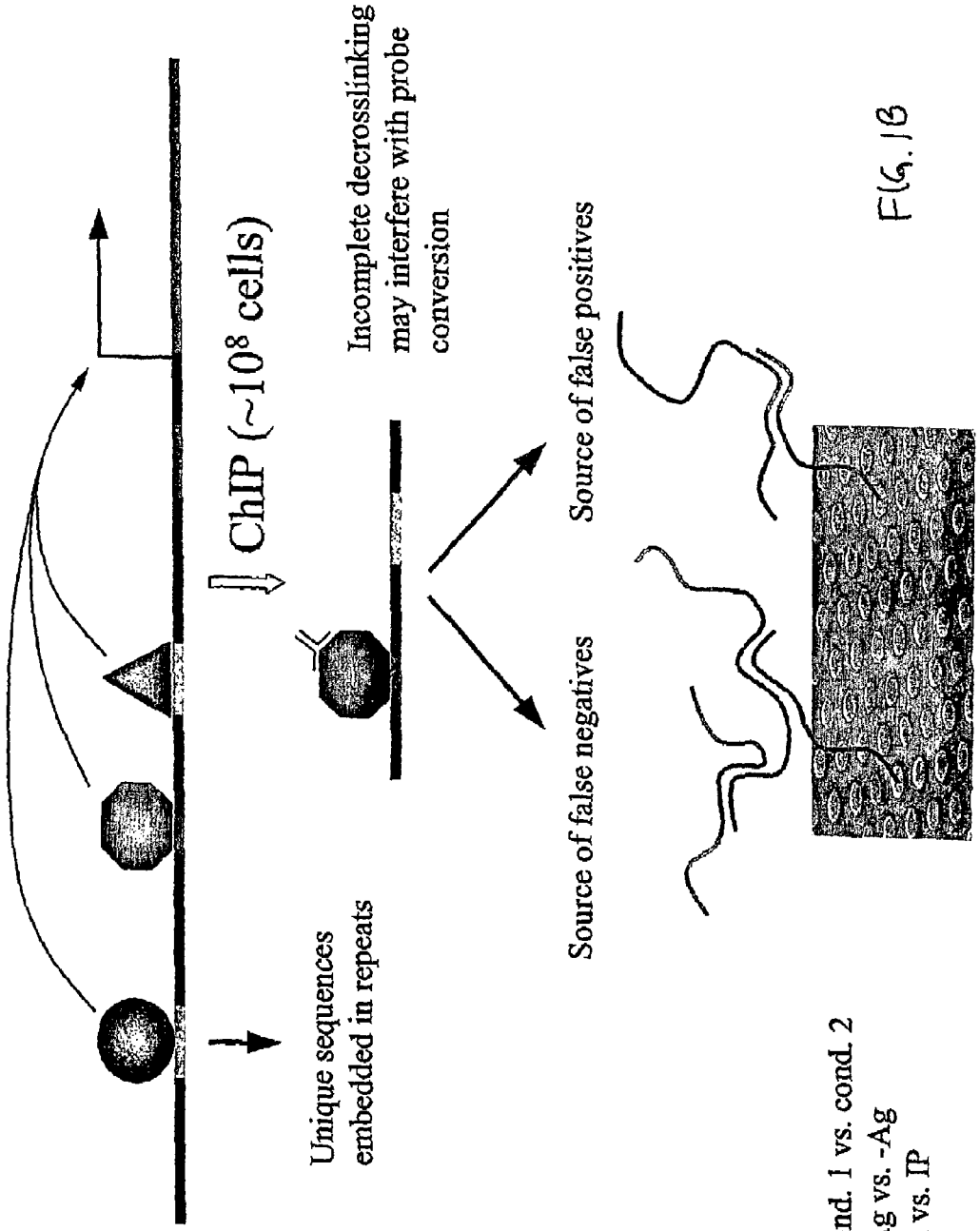

Referring to FIG. 1, in one aspect, the method combines a modified Chromatin Immunoprecipitation (ChIP) procedure with DNA microarray analysis. Polynucleotides (e.g. DNA) and proteins are crosslinked (e.g., cells are fixed with formaldehyde), harvested by sonication, and polynucleotide fragments that are crosslinked to a binding protein or protein of interest are enriched, for example, by immunoprecipitation with a specific antibody. After reversal of the crosslinking, the enriched polynucleotide is contacted with a primer pair under conditions whereby the primer pair hybridizes to the polynucleotide fragment to form a first hybridization complex, each primer comprising at least two portions, a first portion comprising a target-specific oligonucleotide that is capable of hybridizing to a target polynucleotide, and a second portion comprising a universal primer landing site, the two primers are designed to be specific for an upstream and downstream segment of a polynucleotide fragment, one primer of the pair of primers comprising a first universal primer landing site and the second primer comprising a second universal primer landing site, wherein the universal landing sites are not the same. The first hybridization complex is contacted with a ligase under conditions whereby primer pairs hybridized to the polynucleotide fragment are ligated to form a ligated probe. The ligated probes are amplified with universal primers to generate an amplified-labeled product. For example, the amplification can take place using a fluorescent dye and ligation-mediated PCR (LM-PCR). In another embodiment, polynucleotides that have not been enriched by (e.g., immunoprecipitation) is also subjected to LM-PCR in the presence of a different fluorophore, and both enriched and unenriched pools of labeled-product are hybridized to a DNA microarray (as discussed further herein). The enriched/unenriched ratio of fluorescence intensity obtained from a plurality of independent experiments can be used with a weighted average analysis method to calculate the relative binding of a binding protein (e.g., the polypeptide of interest) to each sequence represented on the array.

In the methods of the disclosure proteins that bind a polynucleotide are crosslinked using crosslinking techniques known in the art (e.g., UV light, psorelan and/or formaldehyde). The resulting mixture will comprise both protein bound polynucleotides and polynucleotides that are not bound by protein.

The mixture is then treated to fractionate polynucleotides in the mixture. Fractionation techniques are known in the art and include, for example, shearing techniques to generate smaller genomic fragments. Fragmentation can be accomplished using established methods for fragmenting chromatin, including, for example, sonication, shearing and/or the use of restriction enzymes. The resulting fragments can vary in size. In one aspect, using sonication techniques, fragments of approximately 200-400 nucleotides can be obtained. As a result, polynucleotides fragments crosslinked to binding proteins (e.g., protein-DNA complexes) are generated.

Protein-polynucleotide complexes/fragments can be removed from the mixture by precipitation techniques. Such techniques include, for example, the use of antibodies to protein targets in the mixture. For example, immunoprecipitation using an antibody (e.g., polyclonal, monoclonal) or antigen binding fragment thereof, which binds (specifically) to a binding protein of interest, can be used. In addition, the protein of interest can be labeled or tagged using, for example, an antibody epitope (e.g., hemagglutinin (HA)). The resulting substantially purified (i.e., enriched) crosslinked protein-polynucleotide fragments are then treated to separate the binding proteins from the polynucleotide. The polynucleotide fragment is then combined with oligonucleotide probes comprising a sequence complementary to the polynucleotide fragment under conditions in which hybridization between the polynucleotide fragments and the oligonucleotide primers occurs.

The methods of the disclosure also provide the ability to determine whether a binding protein is a transcription factor. As discussed above, the polynucleotide to which the binding protein interacts are hybridized to DNA fragments (e.g., on a chip). If a polynucleotide binds to a DNA fragment on a chip and the DNA fragment on the chip is known to be a regulatory region in the genome of the organism, then the polynucleotide is identified as a regulatory region and the protein of interest is a transcription factor.

A plurality of probes (also referred to herein as "hybridization probes") comprise at least two portions: a first portion comprises a target-specific oligonucleotide that is capable of hybridizing to a target polynucleotide, and a second portion comprising a "universal primer landing site". Two different hybridization probes are designed to be specific for an upstream and downstream segment of a target polynucleotide. An upstream hybridization probe will comprise a first universal primer landing site and the downstream hybridization probe will comprise a second universal primer landing site. The first and second universal landing sites are not the same. Examples of universal primer landing sites include the T7 and T3 universal primer landing sites. In one aspect of the disclosure, the first universal primer landing site is a T7 primer landing site and the second universal primer landing site is a T3 primer landing site.

These hybridization probes are hybridized to the enriched polynucleotides obtained by ChIP, from a sample, without prior amplification, to form a first hybridization complex. Probes and primers of the disclosure are designed to have at least a portion be substantially complementary to a target polynucleotide, such that hybridization of the target polynucleotide and the probes or primers of the disclosure occurs. As outlined below, this complementarity need not be perfect; there may be any number of base pair mismatches which will interfere with hybridization between the target polynucleotide and the single stranded hybridization probe of the disclosure. Thus, by "substantially complementary" herein is meant that the probes are sufficiently complementary to the target polynucleotide to hybridize under moderate to high stringency conditions.

Thus, the assays are generally run under stringency conditions, which allows formation of the first hybridization complex only in the presence of target. Stringency can be controlled by altering a step parameter that is a thermodynamic variable, including, but not limited to, temperature, formamide concentration, salt concentration, chaotropic salt concentration, pH, organic solvent concentration, and combinations thereof.

These parameters may also be used to control non-specific binding, as is generally outlined in U.S. Pat. No. 5,681,697. Thus it may be desirable to perform certain steps at higher stringency conditions to reduce non-specific binding.

A variety of hybridization conditions may be used in the disclosure, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength and pH. The Tm is the temperature (under defined ionic strength, pH and nucleic acid concentration) at which 50% of the probes complementary to the target hybridize to the polyadenylated mRNA target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of helix destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

Complementary polynucleotides (e.g. DNA) to that of the enriched polynucleotide fragment to which a protein binds (e.g., the protein of interest binds) can be hybridized using a variety of methods. For example, the complementary molecule can be immobilized on a glass slide (e.g., Corning Microarray Technology (CMT™) GAPS™) or on a microchip. Conditions of hybridization will typically include, for example, high stringency conditions and/or moderate stringency conditions. (See e.g., pages 2.10.1-2.10.16 (see particularly 2.10.8-11) and pages 6.3.1-6 in Current Protocols in Molecular Biology). Factors such as probe length, base composition, percent mismatch between the hybridizing sequences, temperature and ionic strength influence the stability of hybridization. Thus, high or moderate stringency conditions can be determined empirically, and depend in part upon the characteristics of the polynucleotide (DNA, RNA) and the other nucleic acids to be assessed for hybridization. Generally, stringent conditions are selected to be about 5-10° C. lower than the thermal melting point ($T_m$) for the specific sequence at a defined ionic strength and pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts), at pH 7.0 to 8.3 and the temperature is at least about 30° C. for short probes (e.g., 10 to about 50 nucleotides) and at least about 60° C. for long probes (e.g., greater than about 50 nucleotides). Stringent conditions may also be achieved with the addition of destabilizing agents such as formamide. For selective or specific hybridization, a positive signal (e.g., identification of a nucleic acid) is about 2 times background hybridization. For the purpose of this disclosure, moderately stringent hybridization conditions mean that hybridization is performed at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL probe, while the washes are performed at about 50° C. with a wash solution containing 2×SSC and 0.1% sodium dodecyl sulfate. Highly stringent hybridization conditions mean that hybridization is performed at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% Dextran sulfate, and 1-15 ng/mL probe, while the washes are performed at about 65° C. with a wash solution containing 0.2×SSC and 0.1% sodium dodecyl sulfate.

The size of the primer and probe may vary, as will be appreciated by those in the art with each portion of the probe and the total length of the probe in general varying from 5 to 500 nucleotides in length. Each portion is between 10 and 100, between 15 and 50 and from 10 to 35 being typically used depending on the use and amplification technique. Thus, for example, the universal priming sites of the probes are each about 15-25 nucleotides in length, with 20 being used most frequent. The adapter sequences of the probes are from 5-25 nucleotides in length, with 10-20 being most common. The target specific portion of the probe is typically from 15-50 nucleotides in length, with from 20 to 40 being most common.

Accordingly, the disclosure provides a first hybridization probe set. By "probe set" herein is meant a plurality of hybridization probes that are used in a particular multiplexed assay. In this context, plurality means at least two, but can include more than 10, depending on the assay, sample and purpose of the test.

Accordingly, the disclosure provides hybridization probe sets that comprise universal priming sites. By "universal priming site" herein is meant a sequence of the probe that will bind a PCR primer for amplification. Each probe set comprises an upstream universal priming site (UUP) and a downstream universal priming site (DUP). Again, "upstream" and "downstream" are not meant to convey a particular 5'-3' orientation, and will depend on the orientation of the system. Typically, only a single UUP sequence and a single DUP sequence is used in a probe set, although as will be appreciated by those in the art, different assays or different multiplexing analysis may utilize a plurality of universal priming sequences. In addition, the universal priming sites are typically located at the 5' and 3' termini of the hybridization probe set (or the ligated probe), as only sequences flanked by priming sequences will be amplified.

In addition, universal priming sequences are generally chosen to be as unique as possible given the particular assays and host genomes to ensure specificity of the assay. In general, universal priming sequences range in size from about 5 to about 35 basepairs, with from about 15 to about 20 being typical.

As will be appreciated by those in the art, the orientation of the two priming sites is different. That is, one PCR primer will directly hybridize to the first universal priming site, while the other PCR primer will hybridize to the complement of the second universal priming site. Stated differently, a first universal priming site is in sense orientation, and a second universal priming site is in antisense orientation.

In addition to the universal priming sites, each hybridization probes of the probe set comprise at least a first target-specific sequence. As will be appreciated by those in the art, the target-specific sequence may take on a wide variety of formats, depending on the use of probe. For example through a primer selection program, a specific 40-mer oligonucleotides can be selected to represent a given region (such as promoter) in the human genome. The process will verify its uniqueness by allowing at least 4 evenly distributed mismatches in related sequences in the genome after the BLAST search against the human genome database(s). Selected sequences also avoid small repeats, have a $T_m$ in a defined range (e.g., between about 55 and 65° C.), and contain minimized secondary structure (calculated by 66 G). In parallel, amino-derived oligos will be synthesized and spotted onto a substrate (e.g., a Motorola 3D codelink slide) to form an oligo-based array (e.g., a promoter array). The oligomer is essentially split in two (e.g., where the oligomer is a 40-mer it is split in two to provide two 20-mers) to provide target specific sequences that are combined with universal primers and thus become the upstream and downstream hybridization probes.

The two hybridization probes can be used in OLA assay systems. The basic OLA method can be run at least two different ways; in a first embodiment, only one strand of a target sequence is used as a template for ligation; alternatively, both strands may be used; the latter is generally referred to as Ligation Chain Reaction or LCR. See generally U.S. Pat. Nos. 5,185,243 and 5,573,907; EP 0 320 308 B1; EP 0 336 731 B1; EP 0 439 182 B1; WO 90/01069; WO 89/12696; and WO 89/09835, all of which are incorporated by reference. The discussion below focuses on OLA, but as those in the art will appreciate, this can easily be applied to LCR as well.

In this embodiment, the hybridization probes comprise at least a first hybridization probe and a second hybridization probe. The method is based on the fact that two probes can be ligated together, if they are hybridized to a target polynucleotide and if perfect complementarity exists at the junction between the two probes, this does not mean that perfect complementarily must exist across the full length of both probes.

In one embodiment, the two hybridization probes are designed each with a target specific portion. The first hybridization probe is designed to be substantially complementary to a first target domain of a target polynucleotide (e.g., a polynucleotide fragment) and the second hybridization probe is substantially complementary to a second target domain of a target polynucleotide (e.g., a polynucleotide fragment). In general, each target specific sequence of a hybridization probe is at least about 5 nucleotides long, with sequences of about 15 to 30 being typical and 20 being especially common. In one embodiment the first and second target domains are directly adjacent, e.g. they have no intervening nucleotides. In this embodiment, at least a first hybridization probe is hybridized to the first target domain and a second hybridization probe is hybridized to the second target domain. If perfect complementarity exists at the junction, a ligation structure is formed such that the two probes can be ligated together to form a ligated probe. If this complementarity does not exist, no ligation structure is formed and the probes are not ligated together to an appreciable degree. This may be done using heat cycling, to allow the ligated probe to be denatured off the target polynucleotide such that it may serve as a template for further reactions. The method may also be done using three hybridization probes or hybridization probes that are separated by one or more nucleotides, if dNTPs and a polymerase are added (this is sometimes referred to as "Genetic Bit" analysis).

In this embodiment, the two hybridization probes are not directly adjacent. In this embodiment, they may be separated by one or more bases. The addition of dNTPs and a polymerase are used to "fill in" the gap, followed by the ligation reaction. This allows the formation of the ligated probe.

As will be appreciated by those in the art, nucleic acid analogs find use as primers and probes in the disclosure. In addition, mixtures of naturally occurring nucleic acids and analogs can be made. Alternatively, mixtures of different nucleic acid analogs, and mixtures of naturally occurring nucleic acids and analogs may be made. For example, peptide nucleic acids (PNA) which includes peptide nucleic acid analogs can be used. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched basepairs. DNA and RNA typically exhibit a 2-4° C. drop in $T_m$ for an internal mismatch. With the non-ionic PNA backbone, the drop is closer to 7-9° C. Similarly, due to their non-ionic nature, hybridization of the bases attached to these backbones is relatively insensitive to salt concentration.

A hybridization probe or primer may contain any combination of deoxyribo- and ribo-nucleotides, and any combination of bases, including uracil, adenine, thymine, cytosine, guanine, inosine, xathanine hypoxathanine, isocytosine, isoguanine, and the like. In one embodiment, isocytosine and isoguanine are used in primers and probes as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

Following ligation, the non-hybridized DNA and hybridization probes are then removed. In one aspect, this is accomplished by using a streptavidin support that can specifically retain all biotinylated DNA, including hybrid complexes. For example, in one aspect the polynucleotides of a sample are biotinylated prior to being contacted with the hybridization probes. Thus, prior to, during, or after contact with the hybridization probes the biotinylated polynucleotides undergo solid phase selection by contacting the biotinylated polynucleotide with a streptavidin substrate.

For example, prior to or after ChIP the polynucleotides are biotinylated. Once the polynucleotide-polypeptide complexes are removed from polynucleotides that do not contain polypeptides, the biotinylated polynucleotides are bound to a solid surface through biotin-streptavidin interactions.

In one aspect, once the unhybridized probes are removed, the hybrids are subjected to ligation. The ligated probes can then be simultaneously amplified using universal primers that will hybridize to the upstream and downstream universal priming sequences. The resulting amplicons, which can be directly or indirectly labeled, can then be detected on arrays. This allows the detection and quantification of the target polynucleotides.

For example, once the non-hybridized probes (and additionally other nucleic acid molecules from the sample that are not of interest) are removed, the ligated probes are denatured and the ligated probes are amplified to form amplicons, which are then detected. This can be done in one of several ways, including PCR amplification and rolling circle amplification. In addition, as outlined below, labels can be incorporated into the amplicons in a variety of ways.

Polynucleotides in the methods described herein can be amplified using, for example, ligation-mediated polymerase chain reaction (e.g., see Current Protocols in Molecular Biology, Ausubel, F. M. et al., eds. 1991, the teachings of which are incorporated herein by reference).

Polynucleotides isolated from an immunoprecipitate, as described herein, can be cloned to generate a library and/or sequenced, and the resulting sequences used to populate a database. Polynucleotides adjacent to those detected by this method are also likely to be regulatory regions. These can be identified by mapping the isolated polynucleotide on the genome for the organism from which the chromatin sample was obtained, and optionally entered into one or more databases.

As will be appreciated by those in the art, polynucleotides can be obtained from samples including, but not limited to, bodily fluids (e.g., blood, urine, serum, lymph, saliva, anal and vaginal secretions, perspiration and semen) of virtually any organism, with mammalian samples common to the methods of the disclosure and human samples being typical. The sample may comprise individual cells, including primary cells (including bacteria) and cell lines including, but not limited to, tumor cells of all types (particularly melanoma, myeloid leukemia, carcinomas of the lung, breast, ovaries, colon, kidney, prostate, pancreas and testes); cardiomyocytes; endothelial cells; epithelial cells; lymphocytes (T-cell and B cell); mast cells; eosinophils; vascular intimal cells; hepatocytes; leukocytes including mononuclear leukocytes; stem cells such as haemopoetic, neural, skin, lung, kidney, liver and myocyte stem cells; osteoclasts; chondrocytes and other connective tissue cells; keratinocytes; melanocytes; liver cells; kidney cells; and adipocytes. Suitable cells also include known research cells, including, but not limited to, Jurkat T cells, NIH3T3 cells, CHO, Cos, 923, HeLa, WI-38, Weri-1, MG-63, and the like (see the ATCC cell line catalog, hereby expressly incorporated by reference).

Polynucleotides are prepared from samples using known techniques. For example, the sample may be treated to lyse a cell comprising the target polynucleotide, using known lysis buffers, sonication techniques, electroporation, and the like.

A target polynucleotide includes a polymeric form of nucleotides at least 20 bases in length. An isolated polynucleotide is a polynucleotide that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an automatically replicating plasmid or virus; or into the genomic DNA of a prokaryote or eukaryote, which exists as a separate molecule (e.g., a cDNA) independent of other sequences, as well as genomic fragments that may be present in solution or on microarray chips. The nucleotides of the disclosure can be ribonucleotides, deoxyribonucleotides, or modified forms of either nucleotide. The term includes single and double stranded forms of DNA.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide also includes triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

In some aspects a polynucleotide or oligonucleotide (e.g., a probe, a primer or primer pair) includes DNAs or RNAs as described above that contain one or more modified bases. Thus, DNAs or RNAs with backbones modified for stability or for other reasons are nucleic acid molecules. Moreover, DNAs or RNAs comprising unusual bases, such as inosine, or modified bases, such as tritylated bases, to name just two examples, are polynucleotides or oligonucleotides as the term is used herein.

It will be appreciated that a great variety of modifications have been made to DNA and RNA that serve many useful purposes known to those of skill in the art. Polynucleotides and oligonucleotides include such chemically, enzymatically or metabolically modified forms of polynucleotides, as well as the chemical forms of DNA and RNA characteristic of viruses and cells, including simple and complex cells, inter alia.

A target polynucleotide may also be comprised of different target domains, that may be adjacent (i.e. contiguous) or separated. For example, in OLA techniques, a first hybridization probe may hybridize to a first target domain and a second hybridization probe may hybridize to a second target domain on a target polynucleotide. The domains can be immediately adjacent, or they may be separated by one or more nucleotides. The terms "first" and "second" are not meant to confer an orientation of the sequences with respect to the 5'-3' orientation of the target polynucleotide. For example, assuming a 5'-3' orientation of a target polynucleotide, the first target domain may be located either 5' to the second domain, or 3' to the second domain. In addition, as will be appreciated by those in the art, probes on the surface of an array of oligonucleotides or polynucleotides may be attached in either orientation, such that they have a free 3' end or a free 5' end. In some embodiments, the probes can be attached at one or more internal positions, or at both ends.

Components of the reaction may be added simultaneously, or sequentially, in any order, with typical embodiments outlined below. In addition, the reaction may include a variety of other reagents which may be included in the assays. Such other reagents include salts, buffers, neutral proteins, e.g. albumin, detergents, and the like, which may be used to facilitate optimal hybridization and detection, and/or reduce non-specific or background interactions. Also reagents that otherwise improve the efficiency of the assay, such as protease inhibitors, nuclease inhibitors, anti-microbial agents, and the like, may be used, depending on the sample preparation methods and purity of the polynucleotides.

In addition, in most embodiments, double stranded target polynucleotides are denatured to render them single stranded so as to permit hybridization of primers and other probes. A typical embodiment utilizes a thermal step, generally by raising the temperature of the reaction to about 95° C., although pH changes and other techniques may also be used.

In one embodiment, the amplification technique is the polymerase chain reaction (PCR). PCR is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference.

In general; PCR may be briefly described as follows. A double stranded hybridization complex is denatured, generally by raising the temperature, and then cooled in the presence of an excess of a PCR primer, which then hybridizes to a universal priming site (e.g., a T7 or T3 priming site). A DNA polymerase then acts to extend the primer with dNTPs, resulting in the synthesis of a new strand forming a hybridization complex. The sample is then heated again, to disassociate the hybridization complex, and the process is repeated. By using a second PCR primer for the complementary target strand that hybridizes to the second universal priming site, rapid and exponential amplification occurs. Thus PCR steps are denaturation, annealing and extension. The particulars of PCR are well known, and include the use of a thermostable polymerase such as Taq I polymerase and thermal cycling. Suitable DNA polymerases include, but are not limited to, the Klenow fragment of DNA polymerase I, SEQUENASE 1.0 and SEQUENASE 2.0 (U.S. Biochemical), T5 DNA polymerase and Phi29 DNA polymerase. The polymerase can be any polymerase, but typically will lack 3' exonuclease activity. Examples of suitable polymerase include but are not limited to exonuclease minus DNA Polymerase I large (Klenow) Fragment, Phi29 DNA polymerase, Taq DNA Polymerase and the like. In addition, in some embodiments, a polymerase that will replicate single-stranded DNA (i.e. without a primer forming a double stranded section) can be used.

The reaction is initiated by introducing the ligated probe to a solution comprising a universal primer, a polymerase and nucleotides. A nucleotide is a deoxynucleoside-triphosphate (also called deoxynucleotides or dNTPs, e.g. DATP, dTTP, dCTP and dGTP). In some embodiments, as outlined below, one or more of the nucleotides may comprise a detectable label, which may be either a primary or a secondary label. In addition, the nucleotides may be nucleotide analogs, depending on the configuration of the system. Similarly, the primers may comprise a primary or secondary label.

Accordingly, the PCR reaction requires at least one and typically two PCR primers, a polymerase, and a set of dNTPs. As outlined herein, the primers may comprise the label, or one or more of the dNTPs may comprise a label.

These embodiments also have the advantage that unligated probes need not necessarily be removed, as in the absence of the target, no significant amplification will occur. These benefits may be maximized by the design of the probes; for example, in the first embodiment, when there is a single hybridization probe, placing the universal priming site close to the 5' end of the probe since this will only serve to generate short, truncated pieces in the absence of the ligation reaction.

Labeling of the amplicon can be accomplished in a variety of ways; for example, the polymerase may incorporate labeled nucleotides (dNTPs), or alternatively, the universal primer itself comprises a label.

By "label" or "detectable label" is meant a moiety that allows detection. This may be a primary label or a secondary label. Accordingly, detection labels may be primary labels (i.e. directly detectable) or secondary labels (indirectly detectable).

In one embodiment, the detection label is a primary label. A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Labels can also include enzymes (e.g., horseradish peroxidase, and the like) and magnetic particles. Common labels include chromophores or phosphors but are typically fluorescent dyes. Suitable dyes for use in the disclosure include, but are not limited to, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals"), pyrene, Malacite green, stilbene, Lucifer Yellow, Cascade Blue™, Texas Red, Cy dyes (Cy3, Cy5, and the like), alexa dyes, phycoerythin, bodipy, and others described in the 6th Edition of the Molecular Probes Handbook by Richard P. Haugland, hereby expressly incorporated by reference.

A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, and the like. Secondary labels include, but are not limited to, one of a binding partner pair such as biotin/streptavidin; chemically modifiable moieties; nuclease inhibitors; enzymes such as horseradish peroxidase; alkaline phosphatases; luciferases, and the like.

The secondary label is typically a binding partner pair. For example, the label may be a hapten or antigen, which will bind its binding partner. For example, suitable binding partner pairs include, but are not limited to: antigens (such as proteins (including peptides)) and antibodies (including fragments thereof (FAbs, and the like)); proteins and small molecules, including biotin/streptavidin; enzymes and substrates or inhibitors; other protein-protein interacting pairs; receptor-ligands; and carbohydrates and their binding partners. Nucleic acid—nucleic acid binding protein pairs are also useful. In general, the smaller of the pair is attached to a nucleotide for incorporation into the primer. Typical binding partner pairs include, but are not limited to, biotin (or imino-biotin) and streptavidin, digeoxinin and Abs, and Prolinx™, reagents. For example, the binding partner pair can comprise biotin or imino-biotin and a fluorescently labeled streptavidin. Imino-biotin disassociates from streptavidin in pH 4.0 buffer while biotin requires harsh denaturants (e.g., 6 M guanidinium HCl, pH 1.5 or 90% formamide at 95° C.).

Labeling can occur in a variety of ways, as will be appreciated by those in the art. In general, labeling can occur in one of two ways: labels are incorporated into primers such that the amplification reaction results in amplicons that comprise the labels or labels are attached to dNTPs and incorporated by the polymerase into the amplicons.

The amplified DNA can be fluorescently labeled by including fluorescently-tagged nucleotides in the LM-PCR reaction or by fluorescently labeling the universal primers.

The labeled amplicon DNA is hybridized to a DNA microarray containing spots representing all or a subset (e.g., a chromosome or chromosomes) of the genome. The fluorescent intensity of each spot on the microarray relative to a non-immunoprecipitated control demonstrates whether the DNA binding protein (e.g., a protein of interest) bound to the DNA region located at that particular spot. Hence, the methods described herein allow the detection of protein-DNA interactions across the entire genome.

As discussed above, the disclosure provides methods and compositions useful in the detection of polynucleotides that interact with polypeptide molecules. The process comprises immunoprecipitating polynucleotides that are crosslinked to polypeptides to obtain enriched polynucleotides; dissociating the polypeptide from the polynucleotide; hybridizing a pair of probes each comprising, for example, a 20-mer target sequence and a universal primer to the enriched polynucleotides; ligating the probes to form ligated probes; amplifying the ligated probes using a universal primer comprising a label; and contacting a microarray (e.g. a DNA microarray) with the amplified-labeled product. The amplified products interact (via hybridization) to an array site comprising a substantially complementary polynucleotide sequence to that of the amplified labeled product.

An array composition comprises at least a first substrate with a surface comprising individual sites. By "array" or "biochip" herein is meant a plurality of polynucleotides or oligonucleotides in an array format. The size of the array will depend on the composition and end use of the array. Nucleic acids arrays are known in the art, and can be classified in a number of ways, both ordered arrays (e.g. the ability to resolve chemistries at discrete sites), and random arrays are included. Ordered arrays include, but are not limited to, those made using photolithography techniques (Affymetrix Gene-Chip™), spotting techniques (Synteni and others), printing techniques (Hewlett Packard and Rosetta), three dimensional "gel pad" arrays, and others known in the art. In addition, liquid arrays find use in the methods of the disclosure.

Generally, the array will comprise from two to as many as a billion or more different sequences, depending on the size of the substrate as well as the end use of the array. Thus very high density, high density, moderate density, low density and very low density arrays may be used. For example, very high density arrays comprise from about 10,000,000 to about 2,000,000,000 nucleic acid molecules, about 100,000,000 to about 1,000,000,000 being typical (all numbers being in $cm^2$). High density arrays comprise a range of about 100,000 to about 10,000,000 nucleic acid molecules, with about 1,000,000 to about 5,000,000 being typical. Moderate density arrays range from about 10,000 to about 100,000 being typical, and from about 20,000 to about 50,000 being most common. Low density arrays generally comprise less than 10,000 nucleic acid molecules, with from about 1,000 to about 5,000 being typical. Very low density arrays comprise less than 1,000 nucleic acid molecules, with from about 10 to about 1000 being typical, and from about 100 to about 500 being most common.

By "substrate" or "solid support" is meant any material that can be modified to contain discrete individual sites appropriate for the attachment or association of oligonucleotides, polynucleotides, or other organic polymers and is amenable to at least one detection method. Possible substrates include, but are not limited to, glass and modified or functionalized glass, plastics (including acrylics, polystyrene and copolymers of styrene and other materials, polypropylene, polyethylene, polybutylene, polyurethanes, Teflon, and the like), polysaccharides, nylon or nitrocellulose, resins, silica or silica-based materials including silicon and modified silicon, carbon, metals, inorganic glasses, optical fiber bundles, and a variety of other polymers. In general, the substrates allow optical detection and do not themselves appreciably interfer with optical detection (e.g., do not fluoresce themselves).

Generally the substrate is flat (planar), although as will be appreciated by those in the art, other configurations of substrates may be used as well. For example, three dimensional configurations can be used, for example by embedding beads in a porous block of plastic that allows sample access to the beads and using a confocal microscope for detection. Similarly, the beads may be placed on the inside surface of a tube for flow-through sample analysis to minimize sample volume.

Generally, the array compositions can be configured in several ways. For example, a first substrate comprising a plurality of assay locations (sometimes also referred to herein as "assay wells"), such as a microtiter plate, is configured such that each assay location contains an individual array. That is, the assay location and the array location are the same. For example, the plastic material of the microtiter plate can be formed to contain a plurality of "wells" in the bottom of each of the assay wells.

In another aspect, the number of individual arrays is set by the size of the microtiter plate used. Thus, 96 well, 384 well and 1536 well microtiter plates utilize composite arrays comprising 96, 384 and 1536 individual arrays, although as will be appreciated by those in the art, not each microtiter well need contain an individual array. It should be noted that the composite arrays can comprise individual arrays that are identical, similar or different. That is, in some embodiments, it may be desirable to do the same 2,000 assays on 96 different samples. Alternatively, doing 192,000 experiments on the same sample (i.e. the same sample in each of the 96 wells) may be desirable. Alternatively, each row or column of the composite array could be the same for redundancy/quality control. As will be appreciated by those in the art, there are a variety of ways to configure the system. In addition, the random nature of the arrays may mean that the same population of beads may be added to two different surfaces, resulting in substantially similar but perhaps not identical arrays.

In use the amplified-labeled product (e.g., a labeled amplicon) is exposed to the array comprising the substantially complementary polynucleotide/oligonucleotide as in the hybridization probe(s). The amplified-labeled product (e.g., a labeled amplicon) and polynucleotide/oligonucleotide in the microarray can hybridize (either directly or indirectly) resulting in a change in the optical signal of a particular microarray location.

The invention has been described above, the following specific embodiments are provided to further illustrate the invention. The specific examples below are not meant to limit the scope of the invention.

EXAMPLES

The following procedures were carried in performing the methods of the disclosure:

Crosslinking. Protein was crosslinked to DNA by adding formaldehyde directly to culture medium to a final concentration of 1% and incubate for 10 minutes at 37 C. (For example, add 270 microliters 37% formaldehyde into 10 ml of growth medium on plate). The medium was then aspirated, removing as much medium as possible. Cells were washed twice using ice cold PBS containing protease inhibitors (1 mM phenylmethylsulfonyl fluoride (PMSF), 1 microgram/ml aprotinin and 1 microgram/ml pepstatin A). The cells were scraped into conical tube and pelleted for 4 minutes at 2000 rpm at 4° C. A lysis buffer was added to precipitated SDS with protease inhibitors (inhibitors: 1 mM PMSF, 1microgram/ml aprotinin and 1 microgram/ml pepstatin A). The cell pellet was resuspended in 200 microliters of SDS lysis buffer and incubate for 10 minutes on ice. Note: The 200 microliters of SDS lysis buffer is per $1 \times 10^6$ cells; if more cells are used, the resuspended cell pellet should be divided into 200 microliters aliquots so that each 200 µl aliquot contains ~$1 \times 10^6$ cells.

The resuspeneded/lysed cell pellet was sonicated to shear DNA to lengths between 200 and 1000 basepairs being sure to keep samples ice cold. Eight microliters 5M NaCl was added to reverse crosslink at 65° C. for 4 hours. DNA was recovered by phenol/chloroform extraction.

Phosphorylation. Six ul of non-phosphorylated pooled oligo pool was mixed with 1/10 volume of 5 M NaCl and 2.5 volume of ice-cold ethanol. The mixtures was incubated at −20 C for 30 minutes. The precipitated oligos were pelleted by centrifugation for 30 minutes. The pellet was washed with 70-75% ethanol and centrifuged for 5 minutes. The pellet was dried and dissolved in an adequate volume of TE (10 mM Tris-HCl, 1 mM EDTA, pH 8.0) or $H_2O$.

Biotinylation of reverse-crosslinked DNA. The phenol-chloroform extracted DNA is washed and dissolved in TE 9pH 8.0). To 10 ul DNA, 100 ng of phage 1 DNA and 1 ul (1 ug/ul) of PHOTOPROBE® Biotin (Vector Laboratories) in $H_2O$ was added to a final volume of 20 ul. The mixture was overlaid with mineral oil and heated at 95 C for 10 minute. To the preparation was added 0.1M Tris (pH 9.5) to a final volume of 80 ul. 160 u. of 2-butanol was add to the mixture, vortexed vigorously, and centrifuged to separate the phases. The upper butanol phase was removed and the butanol extraction repeated. The biotinylated DNA was precipitated by adding the following components and mixing: 10 ul of 10 M $NH_4Ac$, 2 ul of 1 M $MgCl_2$, 1 ul glycogen, 150 ul of −20 C ethanol. Incubate at −20 C ethanol. The mixtures was incubated for 15 minutes at −20 C. Pelleted by centrifugation for 30 minutes and washed with 70% ethanol and centrifuged for 5 minutes. The pellet was dried and resuspended in TE.

Annealing. The following components were mixed in PCR tubes: adequate volume of oligo pool to make each oligo's final concentration 200 fmol/reaction, biotinylated sample DNA, 20 ul 2× binding buffer (40 mM Tris-HCl, pH 7.6, 1 M Nacl, 2 mM EDA, 0.1% Tween-80) in a total volume of 40 ul. The mixture is heated to 95 C for 10 minutes, then cooled to 45 C. Samples are kept for 10 minutes and then add 5 ul of streptavidin-coated paramagnetic beads (Seradyne). The samples were then incubated at 45 C for 2 hours.

Selection. The beads are washed twice with 150 ul of wash buffer (20 mM Tris-HCl, pH 7.6, 0.1 M NaCl, 1 mM EDTA, 0.1% Tween-80). The beads were washed with 1×NEB Taq DNA ligase buffer.

Ligation. Thirty-nine ul of 1×NEB Taq ligase buffer and 1 ul (40 U) NEB Taq ligase were added and incubated at 45 C for 1 hours. The beads were washed twice with wash buffer and the ligated oligonucleotide pairs were eluted with 40 ul $H_2O$ by heating at 95 C for 5 minutes.

Amplification. For each reaction: 2.5 ul of 10×AmpliTaq buffer, 1.5 ul of 25 mM $MgCl_2$, 0.5 ul dNTPs, 15 pmoles of each PCR primer, 2-4 ul of sample and 0.4 ul AmpliTaq Gold (5 U/ul) was mixed to a total volume of 25 ul. PCR cycle conditions were 94 C for 10 minutes and then 30 cycles of 94 C 30 seconds, 54 C for 2 minutes, and 72 C for 2 minutes were performed.

To test the specificity of the methods of the disclosure the following experiments were performed:

Plasmid Spiking. Crosslinking selection and reverse crosslinking were performed as above and known in the art. Oligos were phosphorylated as described above.

Oligonucleotides: 20 different oligonucleotide pairs for genomic DNA detection 16 different oligonucleotide pairs for spiking plasmid DNA detection Biotinylation: the same as describe above except for (i) no phage lambda DNA, (ii) 10 μl PHOTOPROBE® Biotin, and (iii) heating for 30 minutes.

Genomic DNA from 293T cells and 4 different plasmid DNA mixture were biotinylated separately.

3) Annealing: the same as above except for: (i) each oligo's final concentration 400 fmol/reaction and (ii) streptavidin-coated tube (Boeringer-Manhein) instead of f streptavidin-coated paramagnetic beads (Seradyne).

The following reactions were performed:

|  | Reaction # | | | | | | | | | |
|---|---|---|---|---|---|---|---|---|---|---|
|  | 1 | 2 | 3 | 4 | 5 | 6 | 7 | 8 | 9 | 10 |
| Genomic DNA (molecules) | 0 | $10^5$ | $10^5$ | $10^5$ | $10^5$ | $10^5$ | 0 | 0 | 0 | 0 |
| Each plasmid DNA (molecules) | 0 | 0 | $10^2$ | $10^3$ | $10^4$ | $10^5$ | $10^5$ | 0 | $10^5$ | $10^5$ |
| Oligos for Genomic DNA (fmol) | 0 | 0 | 0 | 0 | 0 | 0 | 0 | 400 | 400 | 400 |
| Oligos for Plasmid DNA (fmol) | 400 | 400 | 400 | 400 | 400 | 400 | 400 | 0 | 0 | 0 |

Selection: the same as described above.

Ligation: the same as above except for: 1 hour annealing and 2 hour ligation.

Amplification: the same as above.

Figure 3A:
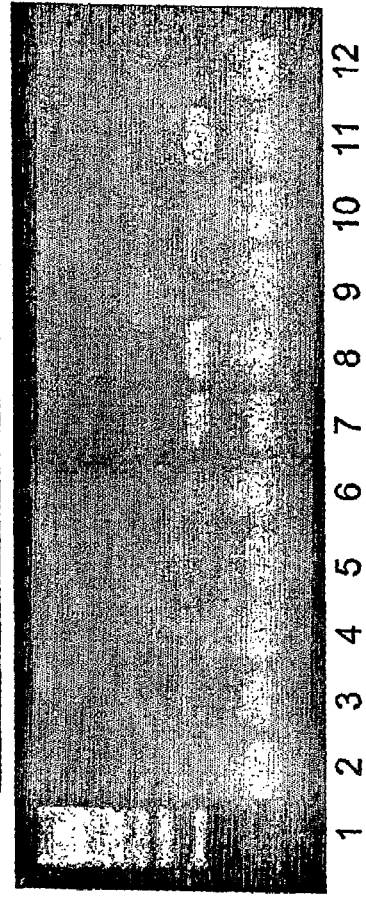
Figure 5:
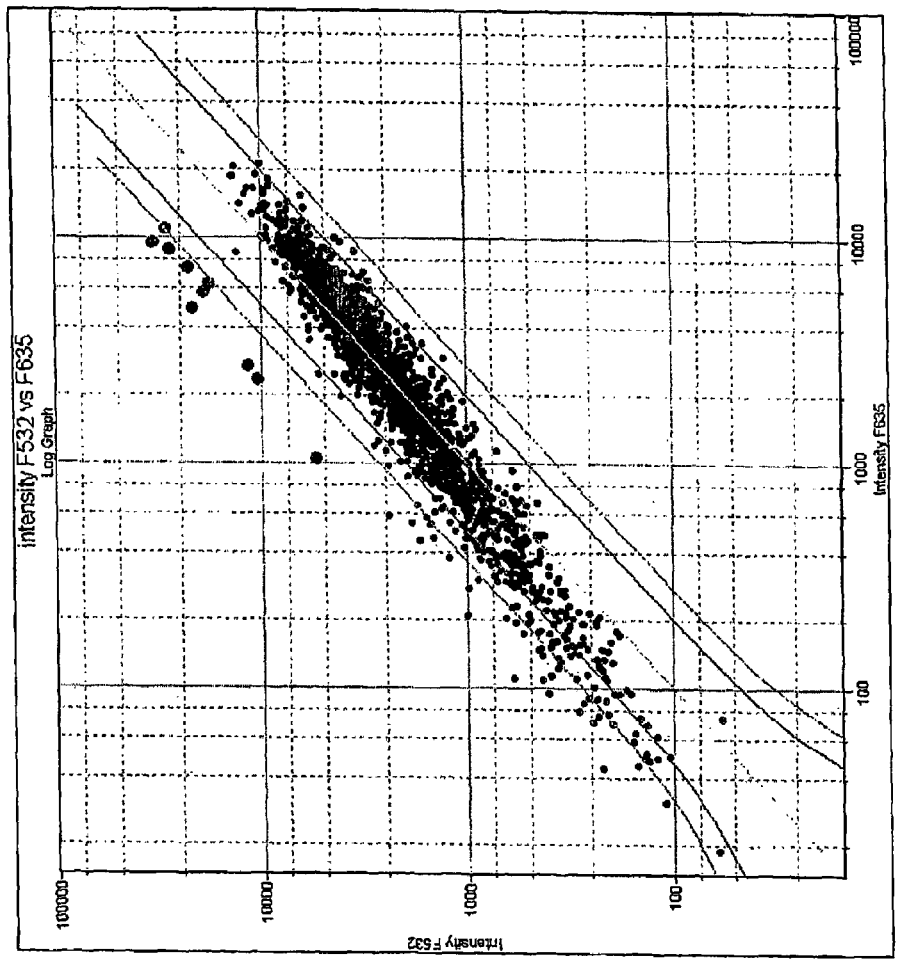
FIG. 5 show results from a 5 fold spiking of 2000 human promoters using the ChIP-DASL assay of the disclosure.

The preparations were analyzed by agarose gel electrophoresis. The data are presented in FIG. 3A.

PCR-fragment spiking experiments with different fold spiking. Oligo phosphorylation was carried out as described above. Oligonucleotides: 15 different oligonucleotide pairs for unspiked genomic DNA detection and 7 different oligonucleotide pairs for spiking and genomic DNA detection.

Biotinylation: the same as above except for (i) no phage lambda DNA, (ii) 10 μl PHOTOPROBE® Biotin, and (iii) heating for 30 minutes.

The following reactions were performed: Genomic DNA from 293T cells and 7 different PCR DNA fragment mixture were biotinylated together.

|  | Reaction # | | | |
|---|---|---|---|---|
|  | 1 | 2 | 3 | 4 |
| Genomic DNA (molecules) | $10^4$ | $10^4$ | $10^4$ | $10^4$ |
| Each spiked DNA (molecules) | $3 \times 10^4$ | $5 \times 10^4$ | $10^5$ | $2 \times 10^5$ |

Annealing: the same as above except for: (i) each oligo's final concentration 400 fmol/reaction and (ii) streptavidin-coated tube (Boeringer-Manhein) instead of streptavidin-coated paramagnetic beads (Seradyne).

Selection: the same as above.

Ligation: the same as above except for: 1 hour annealing and 2 hour ligation.

Amplification: the same as above.

The data are presented in FIG. 3B.

The methods of the disclosure were carried out on androgen receptor (AR) responsive promoters and controls. Table A shows the promoters and controls used in the experiment.

TABLE A

| AR responsive promoters confirmed by ChIP | AR responsive promoters by functional assays | Control promoters | Plasmid controls |
|---|---|---|---|
| KLK2 | CDK2 | GADPH | pUC-GFP |
| KLK3 | P21 | AARS | pUC-GST |
|  | PSP94 | ASNS | pUC-CAT |

TABLE A-continued

| AR responsive promoters confirmed by ChIP | AR responsive promoters by functional assays | Control promoters | Plasmid controls |
|---|---|---|---|
|  | SC | CYP4B1 | pUC-Neo |
|  | FGF8 | GFI1 |  |
|  | TMPRSS2 | HOXB3 |  |
|  | LCP1 | MAP4K1 |  |
|  | NKX3A | RAB23 |  |
|  | F9 | CCL7 |  |

LNCaP cells, a human prostate cancer cell line, were first treated with the androgen agonist dihydrotestosterone (DHT). Mock-treated and DHT-treated cells were subjected to standard ChIP to obtain anti-androgen receptor (AR)-enriched DNA. The ChIP DNA was individually biotinylated and then subject to DASL analysis. Immunoprecipitated DNA from mock-treated cells was amplified with T3 and Alexa-labeled T7, and that from DHT-treated cells was amplified with T3 and Cy3-lableled T7. The products then were pooled and hybridized to the oligonucleotide array containing probes complementary to the targeted sequences from individual promoters. Because the non-androgen responsive promoters will not be immunoprecipitated by anti-AR antibodies, the signal would be low in both mock-treated and DHT-treated cells, which can not be used to calculate the Cy3/Alexa ratio. A higher Cy3/Alexa ratio indicates a positive interaction between androgen receptor and the promoter I LNCaP cells induced by DHT treatment. Interestingly, five promotes (SC, FGF8, LCP1, NKX3A, and F9) were reported in the literature to be androgen responsive in other cell types, but they did not seem to be androgen responsive in LNCaP cells in the data presented in FIGS. 4 and 6.

FIG. 4 shows the results of methods of the disclosure using androgen responsive promoters in LNCaP cells accompanied by SAM analysis. Each of the gels comprises pairs of input DNA in the presence and absence of androgen (IN+ and IN−) and enriched in the presence and absence of androgen (EN+ and EN−).

FIG. 6 shows identification of estrogen receptor target genes using the methods of the disclosure. Shown is the process in the presence and absence of an estrogen agonist. Also shown is the SAM analysis of the chip data.

Conventional genomic tiling involves placing consecutive overlapping genomic sequence on a chip. This strategy would allow unbiased localization of RNA transcripts in a genome. Indeed by hybridizing total cytoplasmic poly(A) RNA to such tiling arrays, investigators have shown that total RNA appears to hybridize to numerous regions in chromosome 21 and 22, many of which do not even correspond to known transcription units.

Figure 7:
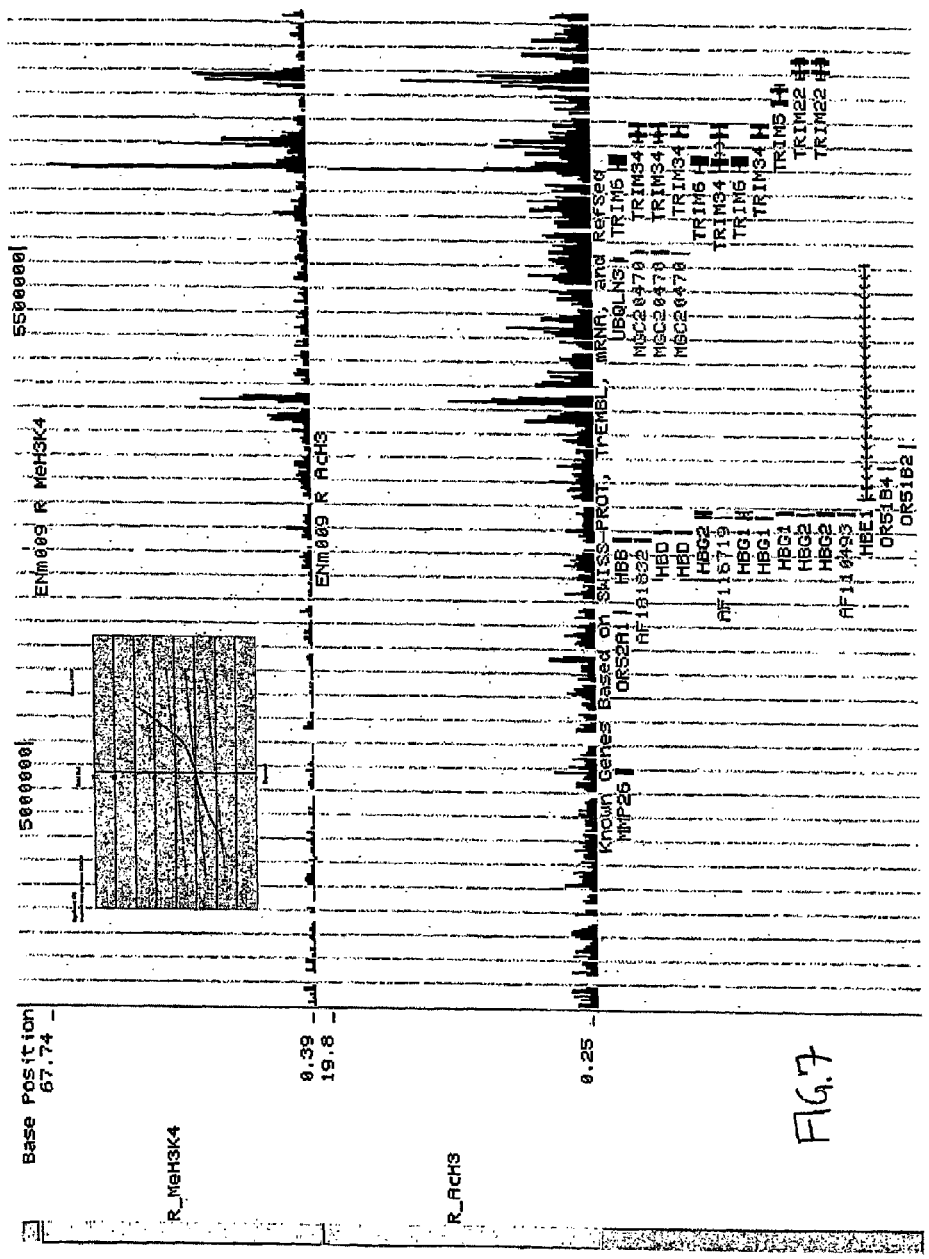
FIG. 7 shows the mapping of transcriptional units using a tiling assay on the beta-globulin locus.
Figure 7:
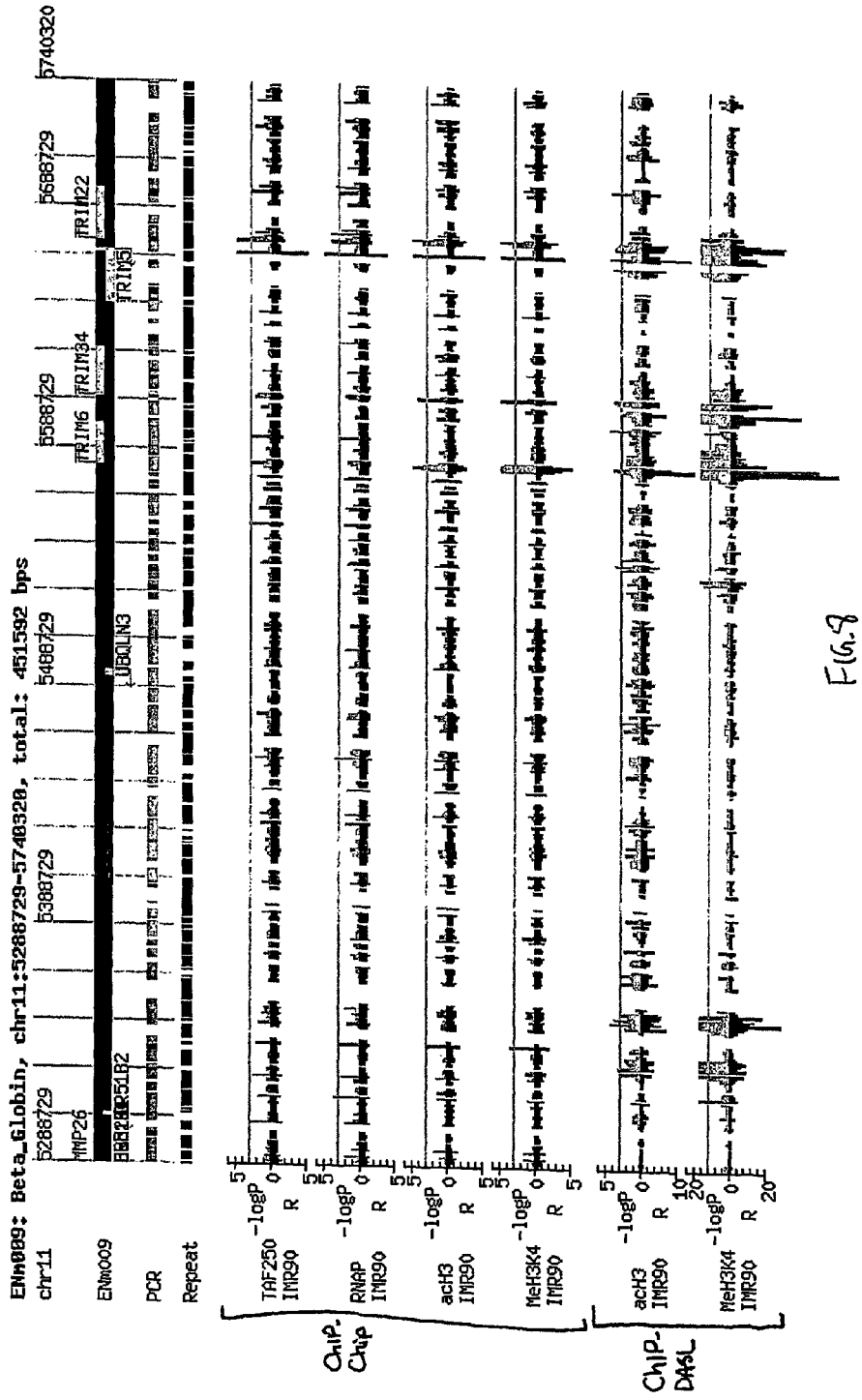
Figure 9:
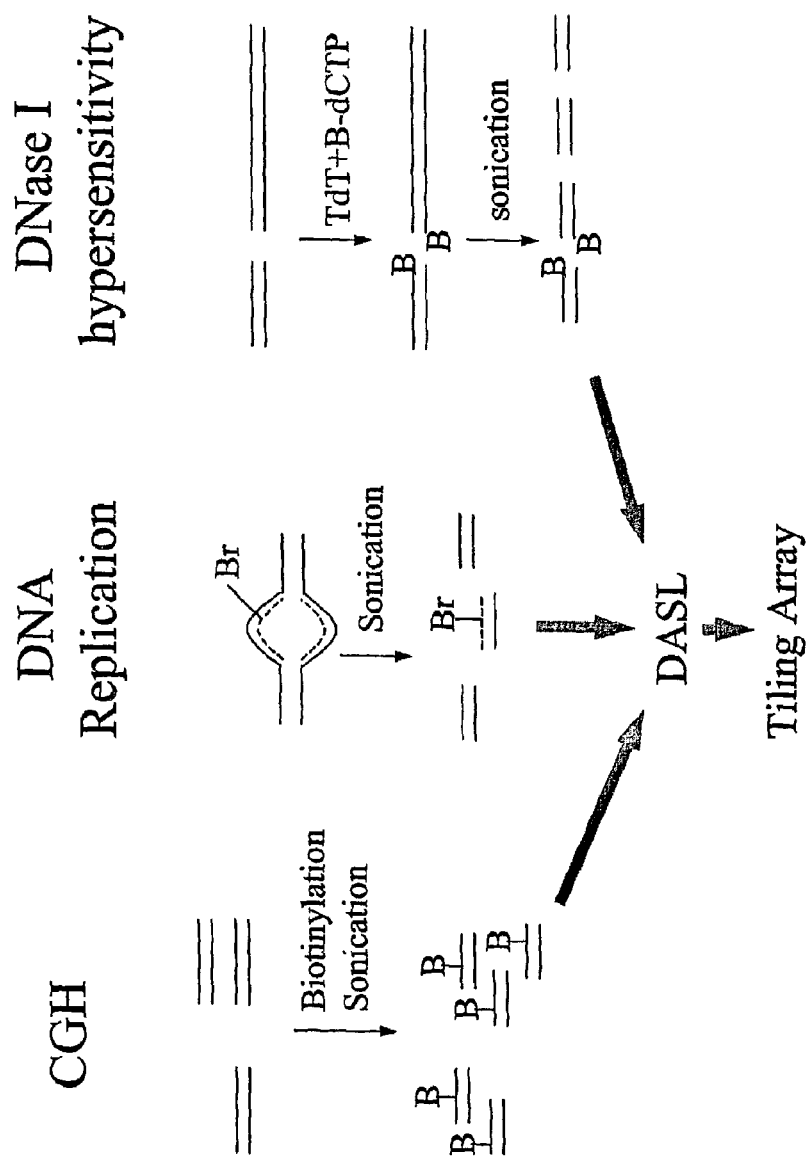
FIG. 9 is a schematic showing the use of the methods of the disclosure on Comparative Genomic Hybridization (CGH), DNA Replication, and DNase I hypersensitivity.

The beta-globulin region in chromosome 11p15 was used to test the combination of tiling with the methods of the disclosure. Using a primer selection program 1000 40-mers were designed to cover the entire 1 Mb region in the beta globin locus. Synthesized oligonucleotide were spotted onto a Motorola 3D CodeLink slide to form a microarray. Corresponding oligonucleotide pairs to each target were prepared and pooled. Data from this experiment is presented in FIGS. 7 and 8.

Based upon the foregoing, the following distinctive advantages of the methods of the disclosure are presented in Table 1.

TABLE 1

Summary: A Comparison

| | ChIP-Chip | ChIP-DASL |
|---|---|---|
| Sensitivity: | $10^8$ cells | $10^6$ cells |
| Fold change detectable | ? | 3–5X |
| Specificity: | ? | High |
| Concerns with repeats | Yes | No |
| Experimental steps: | Many | Fewer |
| De-crosslinking: | Required | Omitted |
| Array format: | PCR products or oligos | Oligos |
| Oligo pool(s): | N/A | Required* |
| Cost per assay (excluding array): | ~$200 | ~$10 |
| Most useful applications: | Promoter & tiling arrays | Promoter & Locus-sp. tiling arrays |

*cost per assay depends on array density and assays to be performed:
For 30K promoter array: $240,000
For 10 labs to perform 1000 assays: $24
For full genome scan: $10 millions
For 10 labs to perform 1000 assays: $1,000

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A method of detecting a polynucleotide-polypeptide interaction domain in a genome of an organism, comprising:
   a) crosslinking polypeptides and polynucleotides in a sample comprising genomic DNA;
   b) fragmenting the sample comprising the crosslinked genomic DNA to obtain polynucleotide fragments;
   c) immunoprecipitating a polynucleotide fragment associated with a polypeptide to obtained an enriched polynucleotide preparation;
   d) biotinylating polynucleotides in the enriched preparation;
   e) contacting the polynucleotide in the enriched preparation with a primer pair under conditions whereby the primer pair hybridizes to the polynucleotide to form a first hybridization complex, each primer comprising at least two portions, a first portion comprising a target-specific oligonucleotide that is capable of hybridizing to a target polynucleotide in the enriched preparation, and a second portion comprising a universal primer landing site, the two primers being specific for an upstream and downstream segment of the target polynucleotide, wherein the universal landing sites are not the same;
   f) contacting the enriched polynucleotide preparation with a substrate comprising streptavidin;
   g) contacting the first hybridization complex with a ligase under conditions whereby primer pairs hybridized to the polynucleotide are ligated to form a ligated probe;
   h) amplifying the ligated probe with universal primers to generate an amplified-labeled product;
   i) contacting the amplified-labeled product with an array of oligonucleotides under conditions whereby the ligated probe hybridizes to a complementary oligonucleotide in the array to form assay complexes; and
   j) detecting the assay complexes, wherein the presence of complexes is indicative of DNA that binds the immunoprecipitated polypeptide.

2. The method of claim 1, wherein the crosslinking of the polynucleotide and polypeptide is performed by UV light, formaldehyde, psorelan, or any combination thereof.

3. The method of claim 1, wherein the universal landing sites are selected from a T3 and T7 priming site.

4. The method of claim 1, wherein the universal primers comprise a detectable label.

5. The method of claim 4, wherein the detectable label is selected from the group consisting of an isotopic label; a magnetic, electrical, or thermal label;
an enzymatic label; and a fluorescent or luminescent label.

6. The method of claim 5, wherein the isotopic label comprises a radioactive or heavy isotopes.

7. The method of claim 5, wherein the fluorescent or luminescent label is selected from the group consisting of fluorescent lanthanide complexes, Europium, Terbium, fluorescein, rhodamine, tetramethylrhodamine, eosin, erythrosin, coumarin, methyl-coumarins, quantum dots, pyrene, Malacite green, stilbene, Lucifer Yellow, pyrenyloxytrisulfonic acid, sulforhodamine 101 chloride, Cyanine dyes, alexa dyes, phycoerythin, and bodipy.

8. A method of detecting a polynucleotide-polypeptide interaction domain in a genome of an organism, comprising:
   a) crosslinking a DNA binding protein to genomic DNA of the organism, thereby producing DNA-protein complexes;
   b) fragmenting the DNA-protein complexes to produce a mixture comprising DNA fragment-protein complexes;
   c) removing a DNA fragment-protein complex from the mixture produced in b) to obtain an enriched polynucleotide-polypeptide preparation;
   d) biotinylating the enriched polynucleotide-polypeptide preparation;
   e) separating the DNA fragment obtained in c) from the DNA binding protein;

f) contacting the DNA of (e) with a primer pair under conditions whereby the primer pair hybridizes to the DNA fragment to form a first hybridization complex, each primer comprising at least two portions, a first portion comprising a target-specific oligonucleotide that is capable of hybridizing to the DNA fragment, and a second portion comprising a universal primer landing site, the two primers designed to be specific for an upstream and downstream segment of the DNA fragment, wherein the universal landing sites are not the same;

g) contacting the DNA comprising biotin with strentavidin;

h) nurifying biotinylated DNA;

i) contacting the first hybridization complex of (h) with a ligase under conditions whereby primer pairs hybridized to the biotinylated DNA fragment are ligated to form a ligated probe;

j) contacting the ligated probe with universal primers;

k) amplifying the ligated probe of i) to obtain an amplified product;

l) combining the amplified product of k) with complementary polynucleotides from the organism under conditions in which hybridization between the amplified product and a region of the complementary polynucleotide occurs to form a second hybridization complex; and m) identifying the second hybridization complex of l), wherein the second hybridization complex comprises the region of the genome to which the DNA binding protein interacts.

9. The method of claim 8, wherein the organism is a eukaryotic cell.

10. The method of claim 8, wherein the organism is a prokaryotic cell.

11. The method of claim 8, wherein the DNA binding protein is a transcription factor.

12. The method of claim 8, wherein the DNA binding protein of the cell is crosslinked to the genomic DNA of the organism using formaldehyde, psorelan, and/or UV light.

13. The method of claim 8, wherein the DNA is fragmented using a restriction enzyme and/or sonication.

14. The method of claim 8, wherein the DNA fragment-protein complex is removed using an antibody which binds to the protein.

15. The method of claim 8, wherein the ligated probe of h) is amplified using ligation-mediated polymerase chain reaction.

16. The method of claim 8, wherein the second hybridization complex is formed on a DNA microarray.

17. The method of claim 8, wherein the universal primer landing sites are selected from a T3 and T7 priming site.

18. The method of claim 8, wherein the universal primers comprise a detectable label.

19. The method of claim 18, wherein the detectable label is selected from the group consisting of an isotopic label; a magnetic, electrical, or thermal label; an enzymatic label; and a fluorescent or luminescent label.

20. The method of claim 19, wherein the isotopic label comprises a radioactive or heavy isotopes.

21. The method of claim 19, wherein the fluorescent or luminescent label is selected from the group consisting of fluorescent lanthanide complexes, Europium, Terbium, fluorescein, rhodamine, tetramethylrhodamine, eosin, erythrosin, coumarin, methyl-coumarins, quantum dots, pyrene, Malacite green, stilbene, Lucifer Yellow, pyrenyloxytrisulfonic acid, sulforhodamine 101 chloride, Cyanine dyes, alexa dyes, phycoerythin, and bodipy.

22. A method of identifying a region of a genome of a living cell to which a polypeptide of interest binds, comprising:

a) crosslinking DNA binding polypeptides in the living cell to genomic DNA of the living cell, thereby producing DNA binding polypeptides crosslinked to genomic DNA;

b) generating DNA fragments of the genomic DNA crosslinked to DNA binding polypeptides, thereby producing DNA fragments to which DNA binding polypeptides are bound;

c) immunoprecipitating a DNA fragment using an antibody that specifically binds a polypeptide of interest;

d) separating the DNA fragment obtained in c) from the polypeptide of interest;

e) biotinylating the DNA fragments of (d);

f) contacting the DNA fragment with a primer pair under conditions whereby the primer pair hybridizes to the DNA fragment to form a first hybridization complex, each primer comprising at least two portions, a first portion comprising a target-specific oligonucleotide that is capable of hybridizing to the DNA fragment, and a second portion comprising a universal primer landing site, the two primers are designed to be specific for an upstream and downstream segment of the DNA fragment, wherein the universal landing sites are not the same;

g) contacting the first hybridization complex with a ligase under conditions whereby the primer pairs hybridized to the DNA fragment are ligated to form a ligated probe;

h) amplifying the ligated probe of g) using universal primers labeled with a detectable label to obtain an amplified product;

i) combining the amplified product of h) with complementary polynucleotides from the cell, under conditions in which hybridization between the amplified product and a region of the complementary polynucleotide occurs to form a second hybridization complex; and j) identifying the second hybridization complex of i) using methods specific for the label, wherein the second hybridization complex comprises the region of the genome in the cell to which the polypeptide of interest binds.

23. The method of claim 22, further comprising comparing the label intensity/amount measured in j) to the amount/intensity of a control, wherein amount/intensity of the label in a region of the genome which is greater than the amount/intensity of label of the control in the region indicates the region of the genome in the cell to which the polypeptide of interest binds.

24. The method of claim 22, wherein the cell is a eukaryotic cell.

25. The method of claim 22, wherein the cell is a prokaryotic cell.

26. The method of claim 22, wherein the DNA binding polypeptide is a transcription factor.

27. The method of claim 22, wherein the DNA binding polypeptide is crosslinked to the genomic DNA of the cell using formaldehyde, psorelan, and/or UV light.

28. The method of claim 22, wherein the DNA is fragmented using a restriction enzyme and/or sonication.

29. The method of claim 22, wherein the ligated probe of f) is amplified using ligation-mediated polymerase chain reaction.

30. The method of claim 22, wherein the second hybridization complex is formed on a DNA microarray.

31. The method of claim 22, wherein the universal primer landing sites are selected from a T3 and T7 priming site.

32. The method of claim 22, wherein the universal primers comprise a detectable label.

33. The method of claim 32, wherein the detectable label is selected from the group consisting of an isotopic label; a magnetic, electrical, or thermal label; an enzymatic label; and a fluorescent or luminescent label.

34. The method of claim 33, wherein the isotopic label comprises a radioactive or heavy isotopes.

35. The method of claim 32, wherein the fluorescent or luminescent label is selected from the group consisting of fluorescent lanthanide complexes, Europium, Terbium, fluorescein, rhodamine, tetramethylrhodamine, eosin, erythrosin, coumarin, methyl-coumarins, quantum dots, pyrene, Malacite green, stilbene, Lucifer Yellow, pyrenyloxytrisulfonic acid, sulforhodamine 101 chloride, Cyanine dyes, alexa dyes, phycoerythin, and bodipy.

* * * * *